US00PP23261P2

(12) United States Plant Patent
Klemm et al.

(10) Patent No.: US PP23,261 P2
(45) Date of Patent: Dec. 18, 2012

(54) NEW GUINEA IMPATIENS PLANT NAMED 'KLENI10128'

(50) Latin Name: *Impatiens hawkeri*
Varietal Denomination: KLENI10128

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/136,221

(22) Filed: Jul. 26, 2011

(51) Int. Cl.
*A01H 5/00* (2006.01)

(52) U.S. Cl. ..... Plt./318.6

(58) Field of Classification Search ..... Plt./318.6, Plt./318.5, 318.1
See application file for complete search history.

(56) References Cited

OTHER PUBLICATIONS http://www.upov.int/pluto/en UPOV, International Union for the Protection of New Varieties of Plants, PLUTO: Plant Variety Database (citation for *New Guinea impatiens* 'kleni10128'.*
Jun. 2011. http://www.upov.int/pluto/en/ UPOV, International Union for the Protection of New Varieties of Plants, PLUTO: Plant Variety Database (citation for New Guinea impatiens 'Kleni10128').*

* cited by examiner

*Primary Examiner* — Howard Locker
(74) *Attorney, Agent, or Firm* — Jondle & Associates, P.C.

(57) ABSTRACT

A new New Guinea *Impatiens* plant named 'KLENI10128', particularly distinguished by its suitability for growth in small pots, high density production, large flowers combined with compact growth and profuse flowering, is described.

1 Drawing Sheet

Genus and species: *Impatiens hawkeri.*
Variety denomination: 'KLENI10128'.

BACKGROUND OF THE NEW PLANT

The present invention comprises a new and distinct variety of New Guinea *Impatiens*, botanically known as *Impatiens hawkeri*, and hereinafter referred to by the variety name 'KLENI10128'. The new variety originated from a hybridization made in November 2007 in Kenya. The female parent was the proprietary *Impatiens* plant 'NI-2006-0100' (unpatented), while the male parent was the proprietary *Impatiens* plant 'NI-2006-0082' (unpatented).

The new variety was first propagated in the Summer of 2008 in Stuttgart, Germany and has been asexually reproduced repeatedly by vegetative cuttings in Stuttgart, Germany for 6 generations. 'KLENI10128' has been found to retain its distinctive characteristics through successive asexual propagations.

Plant Breeder's Rights for this variety were applied for in Switzerland on Jun. 23, 2010 and in the European Union on Jul. 9, 2010. 'KLENI10128' has not been made publicly available more than one year prior to the filing of this application.

SUMMARY OF THE INVENTION

The following are the most outstanding and distinguishing characteristics of this new variety when grown under normal horticultural practices in a glass greenhouse in Stuttgart, Germany 1. Suitability for growth in small pots (such as 10.5 cm) and high density production;
2. Large flowers combined with compact growth; and
3. Profuse flowering.

DESCRIPTION OF PHOTOGRAPH

This New Guinea *Impatiens* plant is illustrated by the accompanying photograph which shows the overall plant habit including blooms, buds, and foliage of the plant. The colors shown are as true as can be reasonably obtained by conventional photographic procedures. Variations in bloom coloration as shown in the accompanying photograph and the stated R.H.S. designations are due to light reflectance and/or shading. The photograph is of a plant about 18 weeks old, grown from rooted cuttings in a 10.5 centimeter pot in a glass-covered greenhouse in April 2010, in Stuttgart, Germany, under conditions which approximate those generally used in normal horticultural practice.

DESCRIPTION OF THE NEW VARIETY

The following detailed descriptions set forth the distinctive characteristics of 'KLENI10128'. The data which defines these characteristics were collected from asexual reproductions carried out in Stuttgart, Germany. The plant history was taken in June 2010, on 18 week old plants which were planted as rooted cuttings in 10.5 cm pots, and then grown in a glass-covered greenhouse in Stuttgart, Germany. Color readings were taken under natural light in the greenhouse. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
*Family.*—Balsaminaceae.
*Botanical name.*—*Impatiens hawkeri.*
*Common name.*—New Guinea *Impatiens.*

Parentage:
*Female parent*.—The proprietary New Guinea *Impatiens* plant, 'NI-2006-0100' (unpatented).
*Male parent*.—The proprietary New Guinea *Impatiens* plant, 'NI-2006-0082' (unpatented).
Growth:
*Growth and branching habit*.—Compact; round.
*Height*.—14.0 cm.
*Width*.—27.0 cm.
*Propagation*.—Vegetative cuttings.
*Time from rooted cutting to finish*.—42 to 49 days in the Spring, when grown in 10 cm pots.
*Time to initiate and develop roots*.—3-4 weeks.
Branches:
*Average number*.—16.
*Length of branches*.—7.0 cm.
*Internode length*.—2.0 cm.
*Diameter of branches*.—0.7 cm.
*Stem color*.—RHS 183D.
Leaves:
*Arrangement*.—Base of the plant: Opposite. Middle and upper section of the plant: Whorled.
*Size*.—Length: 9.0 cm. Width: 3.3 cm.
*Shape*.—Oblong to lanceolate.
*Apex*.—Acuminate.
*Base*.—Acuminate.
*Margin*.—Shallowly serrate.
*Color* (*mature leaves*).—Upper surface: RHS 139A. Lower surface: RHS 139C.
*Color* (*immature leaves*).—Upper surface: RHS 143A. Lower surface: RHS 143C.
*Texture* (*both surfaces*).—Leathery, glossy.
*Venation color*.—Upper surface: RHS 139D. Lower surface: RHS 59C.
*Variegation*.—Absent.
*Petioles*.—Length: 1.5 cm. Diameter: 0.3 cm. Color: Both surfaces: RHS 59C. Texture (both surfaces): Smooth. Fragrance: Absent.
Peduncle:
*Color*.—RHS 58A.
*Size*.—Length: 4.2 cm. Diameter: 0.3 cm.
*Texture*.—Smooth.
Flower buds:
*Shape*.—Ovoid, completely closed: drop shaped.
*Size*.—Length: 1.4 cm. Diameter: 1.2 cm.
*Color*.—RHS 143C.
Inflorescence:
*Blooming habit*.—Continuous.
*Inflorescence type*.—Single flower arranged in clusters arising from the leaf axil; flower positioned above the foliage; flowers face upward and outward; flowers are self-cleaning.
*Number of flowers per node*.—4.
*Flowering season* (*both greenhouse grown and outdoor grown plants*).—April to September or October, depending on temperatures.
*Lastingness of individual blooms on the plant*.—14 to 21 days.
*Fragrance*.—Absent.
Flowers:
*Corolla form*.—Single.
*Number of petals*.—5.
*Shape of corolla*.—Round to oval.
*Corolla size*.—Length: 7.0 cm. Width: 7.0 cm. Depth: 0.5 cm.
Petals:
*Shape*.—Cordate.
*Apex*.—Petals are medium incised in the middle.
*Base*.—Round to acute.
*Margin*.—Entire.
*Size*.—Upper petals: Length: 3.5 cm. Width: 5.0 cm. Lateral petals: Length: 3.5 cm. Width: 4.0 cm. Lower petals: Length: 4.2 cm. Width: 4.0 cm. General color description: Violet.
*Color*.—Both surfaces: RHS 80A, and fading to RHS 82A prior to flower senescence. Eye Zone: RHS 58A.
*Texture* (*both surfaces*).—Satiny, smooth.
Spur:
*Shape*.—Oblong to acute.
*Color*.—RHS 59C.
*Size*.—Length: 5.5 cm to 6.5 cm. Diameter: 0.2 cm. Diameter at proximal end: 0.6 cm. Diameter at distal end: 0.1 cm.
Sepals:
*Quantity per flower*.—3-5.
*Arrangement*.—A large sepal is transformed into the spur. Two of the sepals are clearly separated.
*Lateral sepals*.—Shape: Elliptic acuminate. Length: 1.1 cm. Width: 0.5 cm.
*Lower sepals*.—Shape: Elliptic to round. Length: 1.5 cm. Width: 1.5 cm. Apex: Cuspidate.
*Surface texture* (*both upper and lower surfaces*).—Smooth, glabrous.
*Color*.—Upper surface: RHS 185A. Lower surface: RHS 194B.
Reproductive organs:
*Stamens*.—Number and arrangement: 5 stamens are fused, forming a cap over the ovary. Stamen color (upper surface color): RHS 59D. Anthers color: RHS 155A. Pollen color: RHS 158D.
*Pistils*.—Style and stigma: Hair-like. Arrangement: 5 styles and stigmas fused together; arranged in a circle on top of ovary. Color: RHS 155A. Ovary: Shape: Ovate. Length: 0.6 cm. Color: RHS 137A.
Fruit and seed set: Seed production has not been observed.
Disease and insect resistance: Plants have medium tolerance to red spider mite.
Physiological responses: Not tolerant to temperatures below 10° Celsius; not tolerant to frost; tolerant to low light levels relative to bloom production.

COMPARISON WITH PARENTAL AND COMMERCIAL VARIETIES

'KLENI10128' differs from the female parent 'NI-2006-0100' (unpatented) by having large flowers and good branching, while 'NI-2006-0100' has small flowers and less branching.

'KLENI10128' differs from the male parent 'NI-2006-0082' (unpatented), by having early flowering, and a round shape, while 'NI-2006-0082' has late flowering and V-shaped plant habit.

'KLENI10128' differs from the commercial New Guinea *Impatiens* variety 'Miami' (U.S. Plant Pat. No. 11,700) by having large flowers, good branching and a round shape, while 'Miami' has small flowers, less branching and a V-shaped plant habit.

We claim:

1. A new and distinct variety of New Guinea *Impatiens* plant named 'KLENI10128' as shown and described herein.

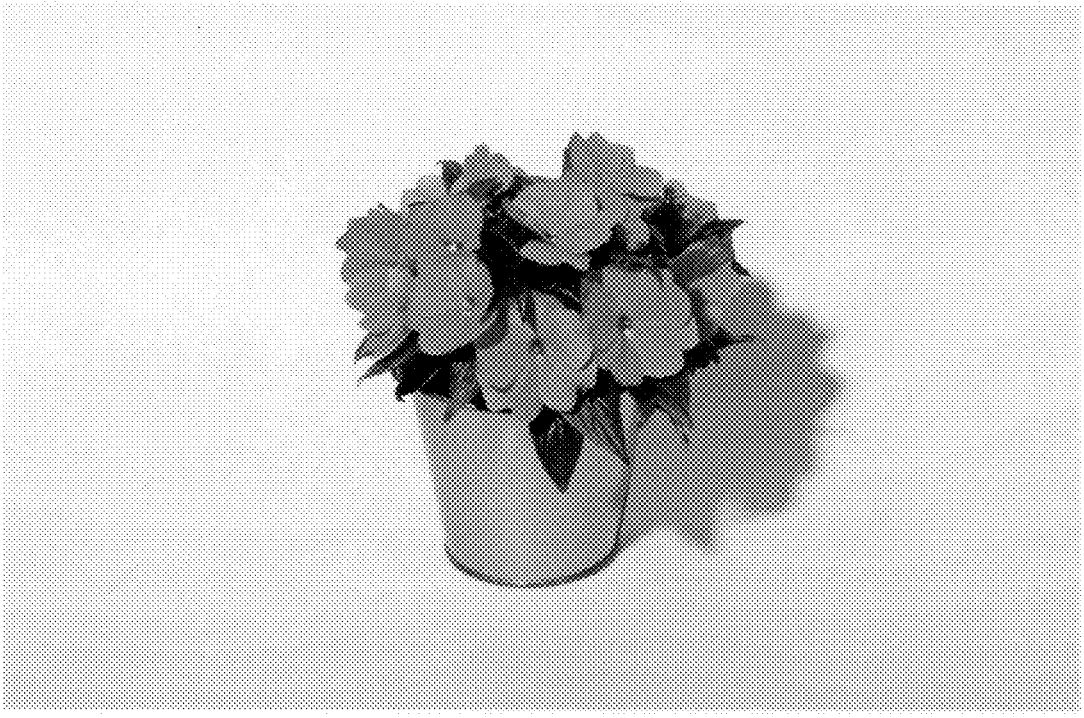

* * * * *